(12) United States Patent
Davagian

(10) Patent No.: US 11,298,515 B2
(45) Date of Patent: Apr. 12, 2022

(54) SINGLE-USE SUPPOSITORY INSERTION DEVICE AND METHOD

(71) Applicant: Cristcot LLC, Concord, MA (US)

(72) Inventor: Jennifer J. Davagian, Acton, MA (US)

(73) Assignee: CRISTCOT LLC, Concord, MA (US)

( * ) Notice: Subject to any disclaimer, the term of this patent is extended or adjusted under 35 U.S.C. 154(b) by 136 days.

(21) Appl. No.: 16/098,623

(22) PCT Filed: May 11, 2017

(86) PCT No.: PCT/US2017/032142
§ 371 (c)(1),
(2) Date: Nov. 2, 2018

(87) PCT Pub. No.: WO2017/197100
PCT Pub. Date: Nov. 16, 2017

(65) Prior Publication Data
US 2019/0143088 A1    May 16, 2019

Related U.S. Application Data

(60) Provisional application No. 62/335,179, filed on May 12, 2016.

(51) Int. Cl.
*A61M 31/00* (2006.01)
*A61M 5/315* (2006.01)
*A61B 17/00* (2006.01)

(52) U.S. Cl.
CPC ... *A61M 31/007* (2013.01); *A61B 2017/0023* (2013.01); *A61M 5/31501* (2013.01)

(58) Field of Classification Search
CPC ............... A61M 31/00; A61M 31/007; A61M 5/31501; A61M 5/31505;
(Continued)

(56) References Cited

U.S. PATENT DOCUMENTS

| 330,764 A | 11/1884 | Worley |
| 504,512 A | 9/1893 | Bailey |

(Continued)

FOREIGN PATENT DOCUMENTS

| CN | 2416896 Y | 1/2001 |
| CN | 201586319 U | * 9/2010 |

(Continued)

OTHER PUBLICATIONS

Banerjee, S. et al., "Inflammatory Bowel Disease Medical Therapy of Specific Clinical Presentations," Gastroenterol Clin N Am, 31: 185-202 (2002).

(Continued)

*Primary Examiner* — Nathan R Price
*Assistant Examiner* — Justin L Zamory
(74) *Attorney, Agent, or Firm* — Hamilton, Brook, Smith & Reynolds, P.C.

(57) ABSTRACT

A single-use suppository insertion device includes a barrel, a plunger to be movably coupled to the barrel, and a disabling feature of the barrel or the plunger. The disabling feature may be activated during operational motion of the plunger relative to the barrel, such as during insertion of or withdrawal away from a suppository. The device can include a structural element of the barrel or the plunger to engage with the disabling feature of the barrel or the plunger during insertion of or withdrawal away from the suppository to activate the disabling feature. The disabling feature may be implemented in a number of ways to ensure single-use operation of the single-use suppository insertion device.

23 Claims, 8 Drawing Sheets

(58) Field of Classification Search
CPC ........... A61M 2005/31506; A61M 2005/5033; A61M 25/0631; A61B 2017/0023; A61J 3/08; A61K 9/02; A61K 9/025
See application file for complete search history.

(56) References Cited

U.S. PATENT DOCUMENTS

| | | | |
|---|---|---|---|
| 2,281,600 A | 5/1942 | Ross |
| 2,290,571 A | 7/1942 | Peyton |
| 2,443,207 A | 6/1948 | Tedford |
| 2,503,445 A | 4/1950 | Lermer |
| 2,532,598 A | 12/1950 | Boeger |
| 2,680,442 A | 6/1954 | Linzmayer |
| 2,709,436 A | 5/1955 | Lynn |
| 2,754,823 A | 7/1956 | Miller |
| 3,015,332 A | 1/1962 | Brecht |
| 3,139,886 A | 7/1964 | Tallman et al. |
| 3,220,413 A | 11/1965 | Sunnen |
| 3,667,465 A | 6/1972 | Voss |
| 3,780,735 A | 12/1973 | Crouter et al. |
| 3,835,856 A | 9/1974 | Warncke |
| 3,840,010 A | 10/1974 | Giglio |
| 4,248,229 A | 2/1981 | Miller |
| 4,341,211 A | 7/1982 | Kline |
| 4,341,221 A | 7/1982 | Testerman |
| 4,361,150 A | 11/1982 | Voss |
| 4,406,655 A | 9/1983 | Clayton |
| 4,421,504 A | 12/1983 | Kline |
| 4,752,288 A | 6/1988 | Hussey |
| 4,990,136 A | 2/1991 | Gcria |
| 5,152,068 A | 10/1992 | Meister et al. |
| D330,764 S | 11/1992 | Lorentzon |
| 5,160,689 A | 11/1992 | Kamen |
| 5,213,566 A | 5/1993 | Weissenburger |
| 5,330,427 A | 7/1994 | Weissenburger |
| 5,352,681 A | 10/1994 | Wittebrood et al. |
| 5,354,325 A | 10/1994 | Chive et al. |
| 5,460,617 A | 10/1995 | Minkus et al. |
| 5,656,283 A | 8/1997 | Brummer et al. |
| 5,662,601 A | 9/1997 | Snead |
| 5,788,664 A | 8/1998 | Scalise |
| 5,860,946 A | 1/1999 | Hofstätter |
| 6,056,714 A | 5/2000 | McNelis et al. |
| D436,661 S | 1/2001 | Berry |
| 6,190,348 B1 | 2/2001 | Tiemann et al. |
| 6,245,776 B1 | 6/2001 | Skwierczynski et al. |
| 6,380,455 B1 | 4/2002 | Moder et al. |
| 6,486,168 B1 | 11/2002 | Skwierczynski et al. |
| 6,500,460 B1 | 12/2002 | Bergeron et al. |
| D471,980 S | 3/2003 | Caizza |
| 6,706,728 B2 | 3/2004 | Hedenstrom et al. |
| 6,740,333 B2 | 5/2004 | Beckett et al. |
| 6,786,883 B2 | 9/2004 | Shippert |
| 6,916,308 B2 | 7/2005 | Dixon et al. |
| 7,070,581 B2 | 7/2006 | Manera et al. |
| 7,081,110 B2 | 7/2006 | Karapasha |
| 7,104,968 B2 | 9/2006 | Swick |
| D529,603 S | 10/2006 | Knickerbocker et al. |
| 7,122,025 B1 | 10/2006 | Nestenborg |
| 7,149,574 B2 | 12/2006 | Yun et al. |
| 7,192,607 B2 | 3/2007 | Bergeron et al. |
| 7,198,612 B2 | 4/2007 | Swick |
| 7,217,252 B2 | 5/2007 | Swick |
| 7,361,168 B2 | 4/2008 | Makower et al. |
| D572,362 S | 7/2008 | Edgett et al. |
| D579,786 S | 11/2008 | Py et al. |
| 7,465,295 B2 | 12/2008 | Bergeron et al. |
| D585,988 S | 2/2009 | Kinnard |
| 7,503,895 B2 | 3/2009 | Rabiner et al. |
| 7,591,808 B2 | 9/2009 | DiPiano et al. |
| D608,659 S | 1/2010 | Py et al. |
| 7,666,160 B2 | 2/2010 | Rajala et al. |
| 8,192,393 B2 | 6/2012 | Ensign |
| 8,419,712 B2 | 4/2013 | Ensign |
| 9,662,481 B2 | 5/2017 | Davagian |
| 10,149,967 B2 | 12/2018 | Davagian et al. |
| 10,525,242 B2 | 1/2020 | Davagian |
| 2002/0048601 A1 | 4/2002 | Beckett et al. |
| 2002/0058674 A1 | 5/2002 | Hedenstrom et al. |
| 2003/0045543 A1 | 3/2003 | Hedenstrom et al. |
| 2003/0088217 A1 | 5/2003 | Bergeron et al. |
| 2003/0233077 A1 | 12/2003 | Swick |
| 2003/0233078 A1 | 12/2003 | Swick |
| 2004/0047910 A1 | 3/2004 | Beckett et al. |
| 2004/0249352 A1 | 12/2004 | Swick |
| 2004/0249416 A1 | 12/2004 | Yun et al. |
| 2004/0260252 A1 | 12/2004 | DiPiano et al. |
| 2005/0004533 A1 | 1/2005 | Smith |
| 2005/0021092 A1 | 1/2005 | Yun et al. |
| 2005/0143378 A1 | 6/2005 | Yun et al. |
| 2005/0143788 A1 | 6/2005 | Yun et al. |
| 2005/0153885 A1 | 7/2005 | Yun et al. |
| 2005/0240241 A1 | 10/2005 | Yun et al. |
| 2005/0256028 A1 | 11/2005 | Yun et al. |
| 2005/0273038 A1 | 12/2005 | Osborn, III et al. |
| 2006/0034847 A1 | 2/2006 | Yun et al. |
| 2006/0035974 A1 | 2/2006 | Yun et al. |
| 2006/0069012 A1 | 3/2006 | Yun et al. |
| 2006/0161105 A1* | 7/2006 | Mori ................... A61M 5/5086 604/110 |
| 2006/0184100 A1 | 8/2006 | Studin |
| 2006/0206149 A1 | 9/2006 | Yun |
| 2007/0073267 A1 | 3/2007 | Muller |
| 2007/0112327 A1 | 5/2007 | Yun et al. |
| 2007/0129668 A1 | 6/2007 | Swick |
| 2007/0185436 A1 | 8/2007 | Swick |
| 2008/0038377 A1 | 2/2008 | Citow |
| 2008/0097286 A1 | 4/2008 | Cleator et al. |
| 2008/0161752 A1 | 7/2008 | Rajala et al. |
| 2008/0167598 A1 | 7/2008 | Gann et al. |
| 2008/0167599 A1 | 7/2008 | Osborn et al. |
| 2008/0300575 A1 | 12/2008 | Cleator et al. |
| 2008/0319269 A1 | 12/2008 | Longo et al. |
| 2010/0010471 A1 | 1/2010 | Ladd et al. |
| 2010/0145379 A1 | 6/2010 | Isham |
| 2013/0204182 A1* | 8/2013 | Ensign ................ A61M 31/007 604/60 |
| 2015/0265820 A1 | 9/2015 | Ensign et al. |
| 2017/0224971 A1 | 8/2017 | Davagian |
| 2019/0151636 A1 | 5/2019 | Davagian et al. |

FOREIGN PATENT DOCUMENTS

| | | | |
|---|---|---|---|
| CN | 201586319 U | 9/2010 | |
| DE | 30 31 408 A1 | 3/1982 | |
| EP | 1 040 808 A2 | 10/2000 | |
| EP | 1 319 420 A1 | 6/2003 | |
| EP | 1 530 978 A1 | 5/2005 | |
| EP | 2554211 A1 * | 2/2013 | ........... A61F 13/266 |
| FR | 1190750 A | 10/1959 | |
| FR | 2923999 A1 | 5/2009 | |
| JP | S59-181834 U | 10/1984 | |
| JP | H02302266 A | 12/1990 | |
| JP | H05-070545 U | 9/1993 | |
| JP | H05-279243 A | 10/1993 | |
| JP | H09-103467 A | 4/1997 | |
| JP | 2001-070456 A | 3/2001 | |
| JP | 2004526520 A | 9/2004 | |
| JP | 2007-215732 A | 8/2007 | |
| JP | 2012-005719 A | 1/2012 | |
| JP | 2012005719 A * | 1/2012 | |
| WO | WO 01/91605 A1 | 12/2001 | |
| WO | 03/101525 A1 | 12/2003 | |
| WO | WO 2004/112755 A1 | 12/2004 | |
| WO | WO 2006/063377 A1 | 6/2006 | |
| WO | WO 2006/077617 A1 | 7/2006 | |
| WO | WO 2008/081353 A1 | 7/2008 | |
| WO | WO 2008/084453 A1 | 7/2008 | |
| WO | WO 2008/102341 A1 | 8/2008 | |

(56) References Cited

FOREIGN PATENT DOCUMENTS

| WO | 2010/042468 A2 | 4/2010 |
|---|---|---|
| WO | 2014/063122 A1 | 4/2014 |

OTHER PUBLICATIONS

Bradshaw, A., "Rectal Suppository Insertion: The Reliability of the Evidence as a Basis for Nursing Practice," Journal of Clinical Nursing, 16: 98-103 (2006).

Fernandez-Becker, N.Q. et al., "Improving Delivery of Aminosalicylates in Ulcerative Colitis," Drugs, 68(8): 1089-1103 (2008).

Hidaka, N. et al., "Changes in the Plasma Diazepam Concentration and Its Anticonvulsant Effect After the Discharge of a Diazepam Suppository from the Rectum in Rats," Methods Find Exp Clin Pharmacol, 29(6): 401-404 (2007).

Howell, H.R., "Ulcerative Colitis: Achieving and Maintaining Remission." US Pharm, 33(12): 30-37 (2008).

Regueiro, M. et al., "Medical Management of Left-Sided Ulcerative Colitis and Ulcerative Proctitis: Critical Evaluation of Therapeutic Trials," Inflamm Bowel Dis, 12(10): 979-994 (Oct. 2006).

Tindall, W.N. et al., "Mild-to-Moderate Ulcerative Colitis: Your Role in Patient Compliance and Health Care Costs," Supplement to Journal of Managed Care Pharmacy, 13(7, S-a): S2-S15 (with attached 2 page Evaluation) (Sep. 2007).

Expedited Review Request, Letter and Attachments A-C from Jennifer Davagian Ensign regarding Expedited Review of 510(k) Premarket Notification, Dated: Sep. 4, 2009.

International Preliminary Report on Patentability for Int'l Application No. PCT/US2017/032142, titled: Single-Use Suppository Insertion Device and Method, date of completion: Nov. 13, 2018.

International Search Report and Written Opinion dated Aug. 29, 2017 for International Application No. PCT/US2017/032142 entitled "Single-Use Suppository Insertion Device and Method".

* cited by examiner

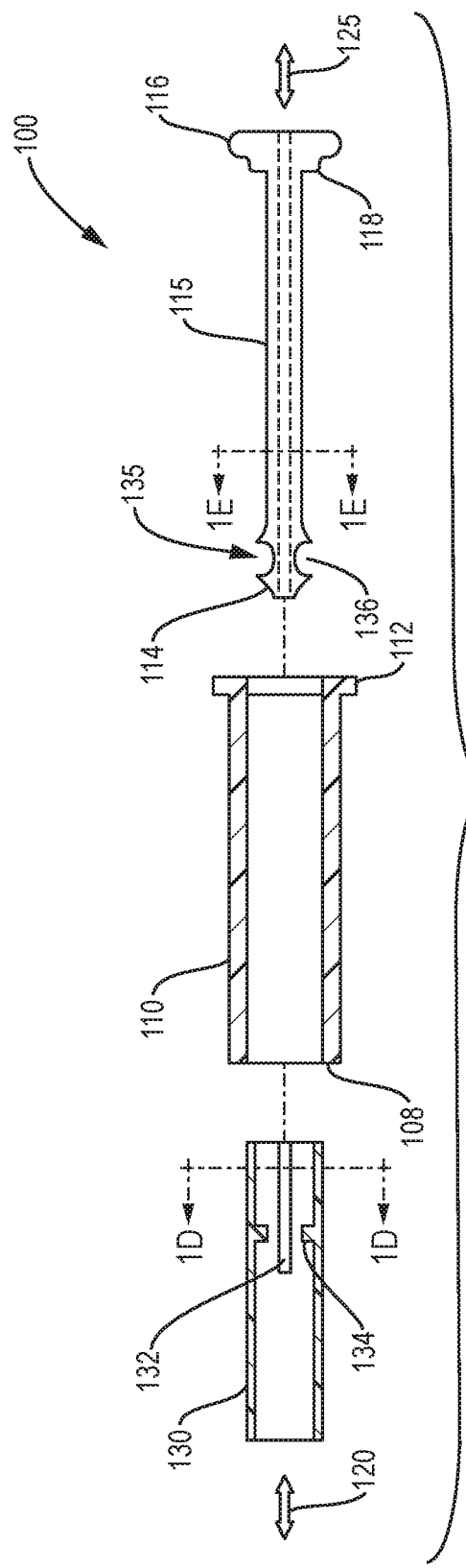
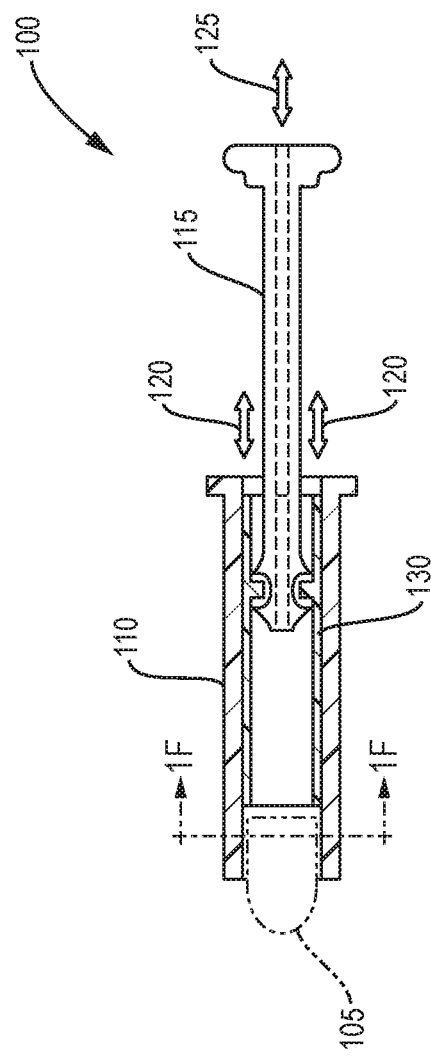
FIG. 1A
FIG. 1B

SINGLE-USE SUPPOSITORY INSERTION DEVICE AND METHOD

RELATED APPLICATION(S)

This application is the U.S. National Stage of International Application No. PCT/US2017/032142, filed May 11, 2017, which designates the U.S., published in English, which claims the benefit of U.S. Provisional Application No. 62/335,179, filed on May 12, 2016. The entire teachings of the above application(s) are incorporated herein by reference.

BACKGROUND

Rectal suppositories are used to administer a predetermined drug dosage to treat a variety of diseases and symptoms. Rectal suppositories are designed to melt inside the body allowing the active pharmaceutical ingredient (API) contained within the rectal suppository to be absorbed by the mucosa lining of the rectum in order to treat a patient locally or systemically. Suppositories are typically used to administer drugs to patients who cannot take the drug orally for a variety of reasons, such as uncontrollable vomiting or nausea, chronic illnesses, and gastrointestinal diseases. In addition, children, the elderly, and patients unable to care for themselves may also use rectal suppositories to treat a variety of symptoms and conditions. In other cases, specific drugs can cause extreme stomach upset or are inactivated in the stomach or liver and are, therefore, better tolerated by rectal administration.

It is common practice to administer rectal suppositories manually using a finger while the patient is, for example, lying on their left side in the fetal position, and after having emptied their bowel. After insertion of the suppository, the patient is instructed to remain on their side in the fetal position for an extended period of time (e.g., at least 30 minutes) while the suppository has time to melt within the rectum and the body begins the absorption process.

Applicators for administering rectal suppositories have been proposed.

SUMMARY OF THE INVENTION

Devices and associated methods for single-use insertion of a suppository are provided.

A method for providing a single-use suppository insertion device according to an example embodiment includes activating a disabling feature of a barrel or a plunger during operational motion of the plunger relative to the barrel, such as during insertion of or withdrawal away from a suppository.

Activating the disabling feature can include engaging, e.g., irreversibly engaging, the disabling feature of the plunger or the barrel with a structural element of the barrel or the plunger. Activating the disabling feature can include activating the disabling feature during insertion of or withdrawal away from a suppository, such as withdrawal of the plunger through the barrel and away from the suppository.

The structural element can include a feature complementary to the disabling feature and can engage the disabling feature with the complementary feature. For example, the complementary feature of the structural element can include a concave surface, and the disabling feature can include a convex surface. The structural element can extend from an inner surface of the barrel, and can be a spacing element, to space the plunger from the barrel.

The disabling feature can be a protrusion extending outward from an outer surface of the plunger. For example, the disabling feature and the structural element can form a ratchet, to allow motion in one direction but prevent motion in another (e.g., opposite) direction.

The structural element can be coupled to or defined by the barrel, and the disabling feature can be coupled to or defined by the plunger. Engaging the disabling feature with the structural element causes the structural element to uncouple from the barrel. For example, a flange can be provided that couples the structural element to the barrel. The flange can be configured to break at a perforation of the flange to cause the structural element to uncouple, which may be a full or partial uncoupling, from the barrel.

The method for providing a single-use suppository insertion device can further include coupling the plunger to an insert receivable in the barrel, the insert including the disabling feature. The plunger can include a fitting to couple to the insert.

A single-use suppository device according to an example embodiment includes a barrel, a plunger configured to be movably coupled to the barrel, and a disabling feature of the barrel or the plunger configured to be activated during operational motion of the plunger relative to the barrel, such as during insertion of or withdrawal away from a suppository.

The single-use suppository insertion device can further include a structural element of the barrel or the plunger configured to engage with the disabling feature of the barrel or the plunger during insertion of or withdrawal away from the suppository to activate the disabling feature.

The structural element, such as a spacing element, fin, protrusion etc., can be configured to maintain a gas flow path associated with the device. The structural element can be configured to engage irreversibly with the disabling feature and can include a feature complementary to the disabling feature. For example, the complementary feature of the structural element can include a concave surface, and the disabling feature can include a convex surface. The structural element can be configured to engage with the disabling feature during withdrawal of the plunger through the barrel.

The device can further include an insert receivable in the barrel and configured to couple to the plunger. The insert can include, or form, the disabling feature. The plunger can include a fitting to couple to the insert, whereby the insert moves with plunger during operational motion of the plunger relative to the barrel. The plunger can further cooperate with the insert to activate the disabling feature.

Another example embodiment of the single-use suppository insertion device may include a barrel, a plunger configured to be movably coupled to the barrel, and means for activating a disabling feature of the plunger or the barrel during operational motion of the plunger relative to the barrel, such as during insertion of or withdrawal away from a suppository.

The means for activating the disabling feature can include a structural element, or equivalents thereof, of the barrel or the plunger configured to engage with the disabling feature of the barrel or the plunger during insertion of or withdrawal away from the suppository.

Embodiments of the present invention can provide several advantages. A disabling feature, which may be provided at the barrel, the plunger, or both, can render the suppository insertion device inoperable after one time use. For example, the disabling feature, once engaged, can prevent retraction of plunger through the barrel, so that the barrel cannot be re-loaded with another suppository. The disabling feature can include a destructive component, such as one or more break-away elements, that renders the insertion device inoperable after one-time use. For example, when the break-away element(s) breaks, the plunger may no longer be engaged with the barrel, leaving the plunger to rattle around in the barrel. In other examples, the disabling feature is irreversibly engaged during operational motion of the plunger relative to barrel. Embodiments can include one or more flow paths that allow gas to flow into or out of the body during insertion of or withdrawal from the suppository, to ensure proper placement of the suppository in the desired anatomical location.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A is a sectional view of a single-use suppository insertion device according to an example embodiment of the invention illustrating the device in an unassembled state;

FIG. 1B is a sectional view of the single-use suppository insertion device of FIG. 1A in an assembled state;

DETAILED DESCRIPTION OF THE INVENTION

Figure 1C:
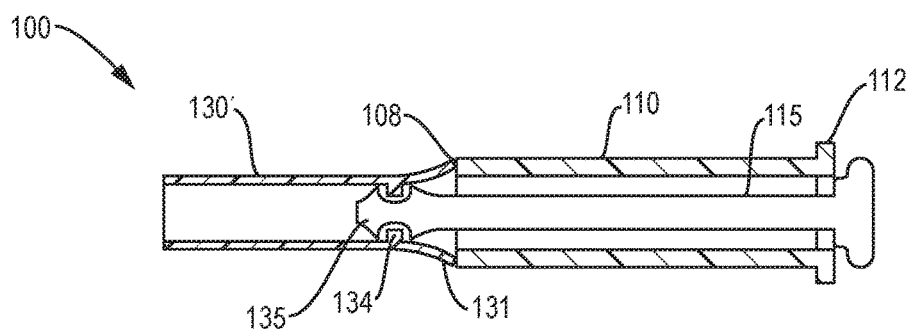
FIG. 1C is a sectional view of the single-use suppository insertion device of FIG. 1B in a locked state, e.g., after insertion of the suppository.
Figure 1D:
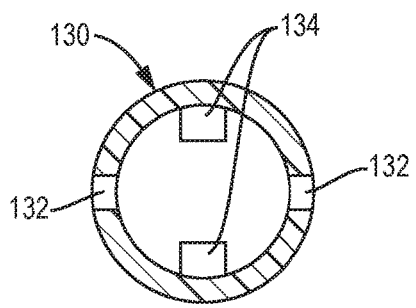
FIG. 1D is a sectional view of the insert of the device of FIG. 1A.
Figure 1E:
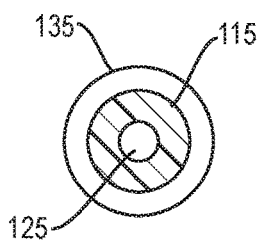
FIG. 1E is a sectional view of the plunger of the device of FIG. 1A.

A description of example embodiments of the invention follows.

Examples of devices and methods for inserting a suppository are described in U.S. Pat. No. 8,192,393, entitled, "Method and Apparatus For Inserting a Rectal Suppository," issued on Jun. 5, 2012, and U.S. Pat. No. 8,419,712, entitled "Method and Apparatus For Inserting a Rectal Suppository," issued on Apr. 16, 2013, the entire teachings of both are incorporated herein by reference.

Further examples of devices for inserting a suppository are described in U.S. patent application Ser. No. 13/840,096, entitled "Method and Apparatus For Inserting a Rectal Suppository," published on Aug. 8, 2013 as U.S. Patent Publication No. 2013/0204182, the entire teachings of which are incorporated herein by reference.

Examples of devices and methods for manufacturing a suppository are described in International Patent Application No. PCT/US2013/065795, entitled "Suppository Insertion Device, Suppository, and Method of Manufacturing a Suppository," published on Apr. 24, 2014 as WO 2014/063122, the entire teachings of which are incorporated herein by reference.

A ratchet is commonly understood to be a locking device or mechanism that permits movement of a part of an apparatus in one direction only, e.g., a lever or spring-loaded catch. A ratchet can include a pawl or detent for preventing backward motion while allowing forward motion of an element of the ratchet.

FIGS. 1A to 1F illustrates an example embodiment of an applicator (insertion device) 100 configured to insert a suppository, e.g., a rectal suppository, 105 into a human or animal according to an embodiment of the present invention. The insertion device 100 is configured for one-time use, as further described below. The device 100 can include means for activating a disabling feature of the plunger or the barrel during operational motion of the plunger relative to the barrel, which may be during insertion of or withdrawal away from a suppository.

As shown in FIG. 1A, the device 100 can include a barrel 110 and a plunger 115. The barrel 110 has a gripping end 112 and an insertion end 108 and can be appropriately sized and shaped to fit within a patient's anal canal. The barrel 110 is further configured to define a gas flow path 120 allowing gas to freely flow through the barrel 110 when positioned within the anal canal. The plunger 115, which has a gripping end (e.g., a finger interface end) 116 and an insertion end 114, is appropriately sized and shaped to extend through the barrel 110. A stepped portion 118 is provided at the gripping end 116 of the plunger. The stepped portion 118 can be configured to ensure that a gas flow path associated with the device 100, e.g., gas flow path 120, is not obstructed during use of the device. The plunger 115 can be configured to be substantially longer than the barrel, thereby allowing the plunger 115 to extend beyond the end of the barrel 110. For example, the barrel 110 may be approximately 4 cm in length whereas the plunger 115 may be approximately 8 cm in length.

Figure 1F:
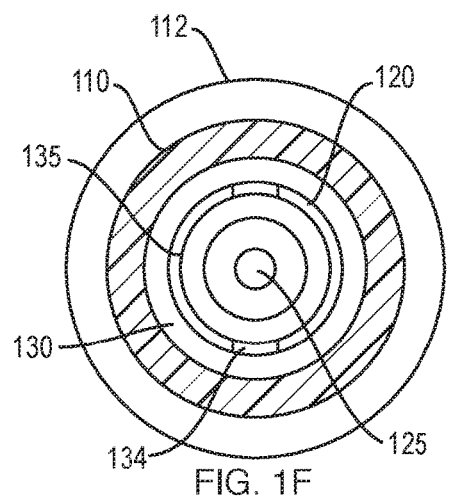
FIG. 1F is a sectional view of the insertion device of FIG. 1B.

As illustrated in FIGS. 1B-1C and 1F, the plunger 115 is configured to be movably (e.g., slidably) coupled to the barrel 110. The plunger 115 may be further configured to maintain a second gas flow path 125 that allows gas to freely flow through the plunger 115 as the plunger is withdrawn from the rectum and anal canal after the suppository 105 has been inserted to a desired position. Thus, as the suppository 105 is being inserted, the barrel 110 maintains a gas flow path 120 allowing gas to escape. As the plunger 115 is being withdrawn, the plunger's gas flow path 125 and the barrel's gas flow path 120 are maintained as the plunger is withdrawn from the suppository 105, and the barrel 110 and plunger 115 are removed from the patient's anal canal. The gas flow paths, 125 and 120, allow gas to escape as the barrel 110 and the plunger 115 are removed from the body preventing or reducing the need to release the gas in the form of flatulence The device 100 can further include an insert 130 receivable in the barrel 110 and configured to couple to the plunger 115. The insert 130 can include, or provide, the disabling feature configured to be activated during operational motion of the plunger 115 relative to the barrel 110, for example, during insertion of or withdrawal away from a suppository. The plunger 115 can include a fitting 135 to couple to the insert 130. In the example shown, the insert 130 includes one or more protrusions 134 that extend inward from an inside wall of the insert. The fitting 135 of the plunger 115 includes one or more complementary features 136 to engage the one or more protrusions 134 of the insert. The fitting 135 is configured to couple to the insert 130 and apply a force to the insert to cause a portion of the insert to expand. The barrel 110 can be configured to restrain expansion of the insert 130, such as while the insert 130 is at least partially within the barrel. Other ways of coupling the plunger 115 to the insert 130 and allowing the insert to expand may be used.

As illustrated in FIGS. 1A-1B, the insert 130 fits within the barrel 110 and allows for gas flow path(s) to be maintained. The insert 130 can be configured to expand, once coupled to the plunger 115, to prevent re-use of the insertion device 100. As illustrated, the insert 130 can include one or more longitudinal slots 132 at one end of the insert. The slots 132 allow the insert 130 to expand, e.g., to flare or increase in circumference. As illustrated in FIG. 1C, when the insert 130 is pushed beyond the insertion end 108 of barrel 110 by action of the plunger 115, the insert expands due to the interaction of the fitting 135 and the insert 130. The expanded insert 130' has a flared end 131 that cannot pass back into the barrel, thereby preventing retraction of the plunger 115 and re-loading of the device 100 with another suppository. The insert 130 can also be manufactured in an expanded state, such as shown in FIG. 1C, and then constrained within the barrel during assembly of the device 100. The insert is allowed to return to its expanded state by action of the plunger 115.

The plunger 115 can engage with the insert 130 before or after loading of the suppository 105. As shown, the fitting 135 is positioned at the insertion end 114 of the plunger 115, but may be positioned anywhere along the length of the plunger.

Figure 2:
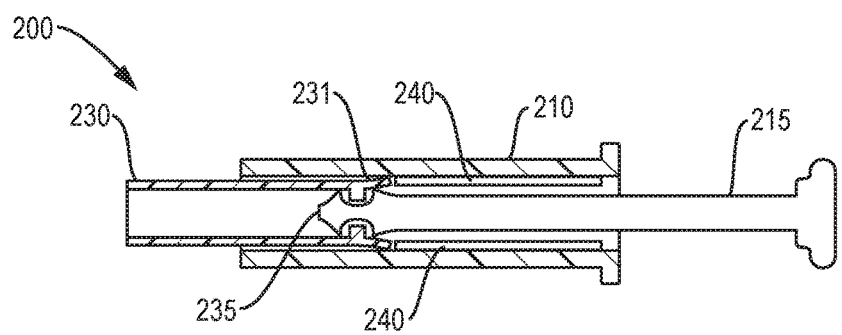
FIG. 2 is a sectional view of a single-use suppository insertion device according to another example embodiment.

In an alternative embodiment of an insertion device 200 illustrated in FIG. 2, the device 200 includes a barrel 210, a plunger 215 and an insert 230. FIG. 2 shows device 200 in a locked state, such as after insertion of a suppository. In the locked state of device 200, the plunger 215 and insert 230 will not move backward. The plunger 215 and insert 230 are similar to the plunger 115 and insert 130 of FIG. 1A. The barrel 210 includes structural elements 240 that extend inwardly. The structural elements 240 can be fins or other spacing elements that are configured to maintain a gas flow path associated with the barrel 210. The insert 230 can be dislodged from a position within the barrel 210, by action of the plunger 215, and can expand at the back end, as illustrated in FIG. 2. The expanded back end 231 of insert 230 engages with the structural elements 240, in a ratchet-like fashion, to prevent backward movement of the insert 230. Because the plunger 215 is coupled to the insert 230, the plunger 215 is also prevented from moving backward, e.g., retracting out of the barrel 210. In this way, the insert 230 cannot be returned to a position within the barrel 210. Thus, the insert 230 provides the disabling feature that, in cooperation with the fins 240, prevents re-use of the device 200.

Figure 3A:
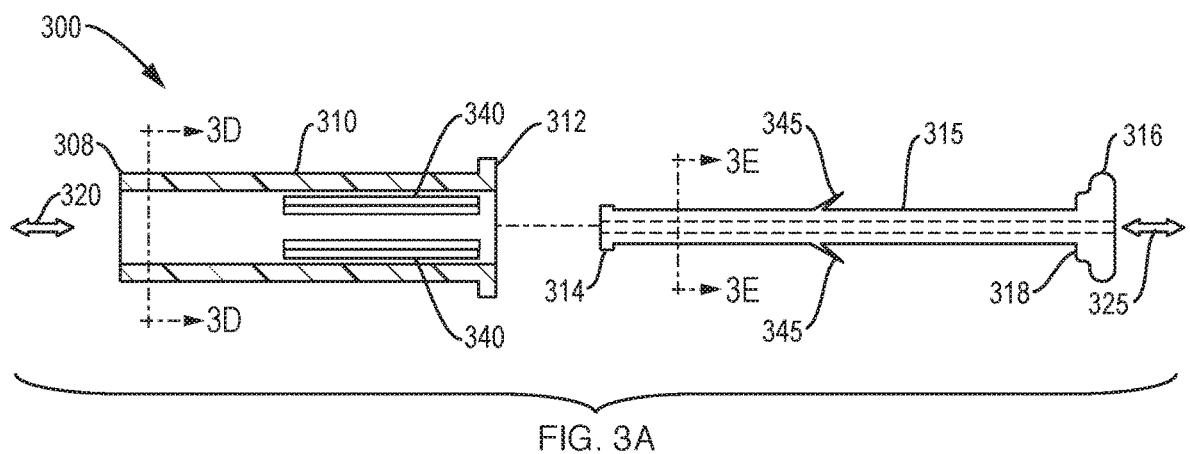
FIG. 3A is a sectional view of a single-use suppository insertion device according to yet another example embodiment of the invention illustrating the device in an unassembled state.
Figure 3B:
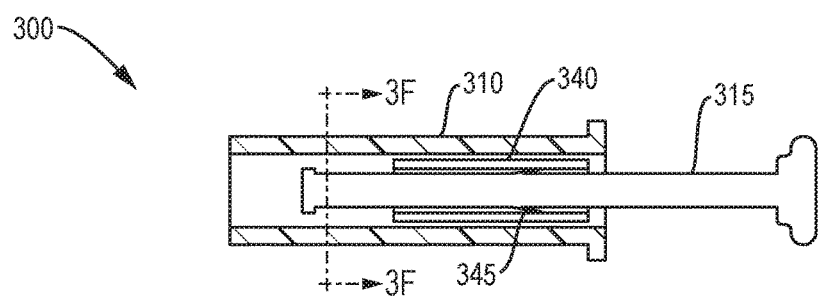
FIG. 3B is a sectional view of the single-use suppository insertion device of FIG. 3A in an assembled state.
Figure 3C:
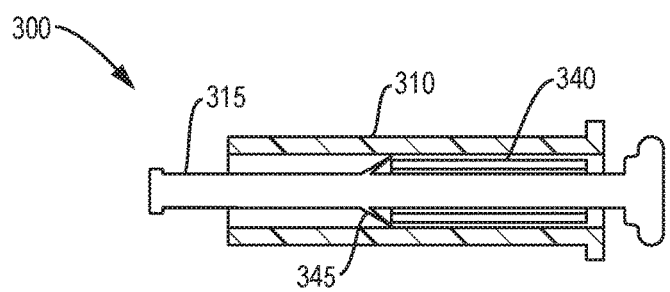
FIG. 3C is a sectional view of the single-use suppository insertion device of FIG. 3B in a locked state, such as after insertion of the suppository.
Figure 3D:
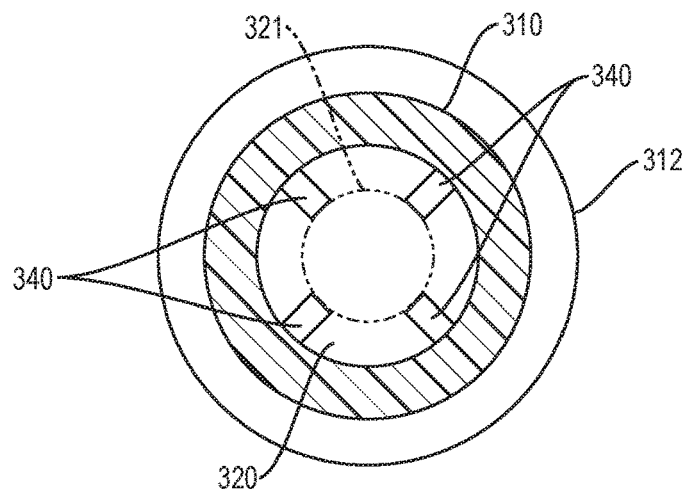
FIG. 3D is a sectional view of the barrel of the device of FIG. 3A.

FIGS. 3A-3F illustrate an alternative embodiment of an insertion device 300 that includes a barrel 310 and a plunger 315 configured to be movably coupled to the barrel. The barrel 310 has an insertion end 308 and a gripping end 312, and further includes structural elements, e.g., fins 340, which can function as spacing elements to maintain a gas flow path 320 associated with the device 300. There may be four fins 340, as illustrated in FIG. 3D, and the fins can provide a space 321 within the barrel 310 for receiving the plunger 315.

As with plunger 115 of device 100, the plunger 315 has a gripping end (e.g., a finger interface end) 316 and an insertion end 314. The plunger 315 is appropriately sized and shaped to extend through the barrel 310. A stepped portion 318 is provided at the gripping end 316 of the plunger 315. The stepped portion 318 can be configured to ensure that a gas flow path associated with the device 300, e.g., gas flow path 320, is not obstructed during use of the device. The plunger 315 can be configured to be substantially longer than the barrel 310, thereby allowing the plunger 315 to extend beyond the insertion end 308 of the barrel 310.

As illustrated in FIG. 3A, one or more flaps 345 are provided that extend outward from an outer surface of the plunger 315. As shown, the flaps 345 can extend outward from plunger 315 at an acute angle and in a direction away from insertion end 314 of the plunger. As exemplified in FIGS. 3A and 3E, there can be two flaps 345. The flaps 345 can be resilient and may be spring-loaded. The flaps 345 can be configured to bend, e.g., elastically deform, when compressed against the plunger 315 by fins 340, such as when the plunger is advanced into the barrel. The flaps 345 can be sized and shaped such that the fins 340 will bend the flaps irrespective of the relative rotation of the plunger and the barrel. FIGS. 3B and 3C illustrate two different stages of advancement of the plunger 315 into barrel 310.

Figure 3E:
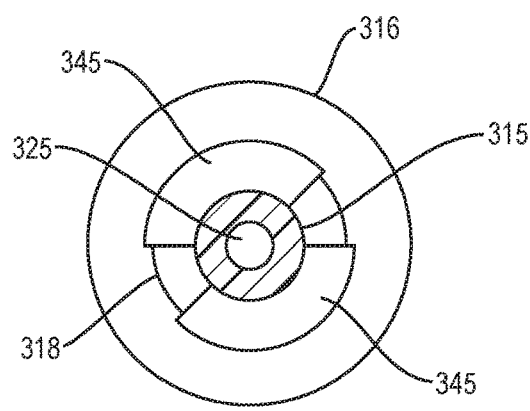
FIG. 3E is a sectional view of the plunger of the device of FIG. 3A.
Figure 3F:
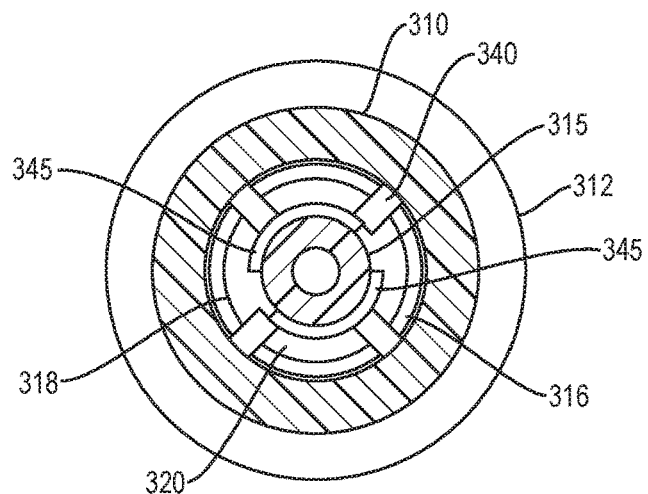
FIG. 3F is a sectional view of the device of FIG. 3B.

As illustrated in FIG. 3B, and in cross-section in FIG. 3F, the flaps 345 are bent and held close to the plunger 315 as they pass through the portion of the barrel 310 that includes the fins 340. As shown in FIG. 3C, the flaps 345 expand after passing past the end of the fin portion of the barrel 310. The expanded flaps 345 engage the fins 340 and prevent retraction of the plunger 315, locking the plunger against the barrel and thereby preventing re-use of the device 300. Thus, the flaps 345 provide a disabling feature that, in cooperation with the fins 340, prevents re-use of the device 300. The fins 340 can include a feature complementary to the flaps 345. For example, the fins can include a concave surface to engage the tips of the flaps 345. The fins 340 and flaps 345 can form a ratchet mechanism.

As with plunger 115, the plunger 315 may be further configured to maintain a second gas flow path 325 (FIGS. 3A and 3E) that allows gas to freely flow through the plunger 315 as the plunger is withdrawn from the rectum and anal canal after the suppository has been inserted to a desired position.

FIG. 3D is a sectional view of the barrel 310 of the device 300 of FIG. 3A. Four fins 340 extend into an inner lumen of the barrel and provide space 321 for the plunger 315.

FIG. 3E is a sectional view of the plunger 315 of the device 300 of FIG. 3A, illustrating the gas flow path 325 that extends through the body of the plunger 315. Also shown are two flaps 345 that extend radially outward from the body of the plunger.

FIG. 3F is a sectional view of the device 300 of FIG. 3B, illustrating a stage of advancement of the plunger 315 into barrel 310, including compression of flaps 345 by fins 340, as described above. Also shown is gas flow path(s) 320, maintained between the plunger 315 and barrel 310.

With any of the single-use insertion devices described herein, a mechanism can be provided to prevent premature advancement of the plunger into the barrel, thus preventing premature activation of the disabling feature. The mechanism can be an insert or a component of the barrel, the plunger, or both. The insert or component can prevent the device from locking prematurely, such as while a user is handling the device, loading the suppository, or at any other time before the suppository has been delivered. The mechanism can include a break-away locking mechanism or a removable clip or cuff, as will be described next with respect to FIGS. 3G and 3H.

Figure 3G:
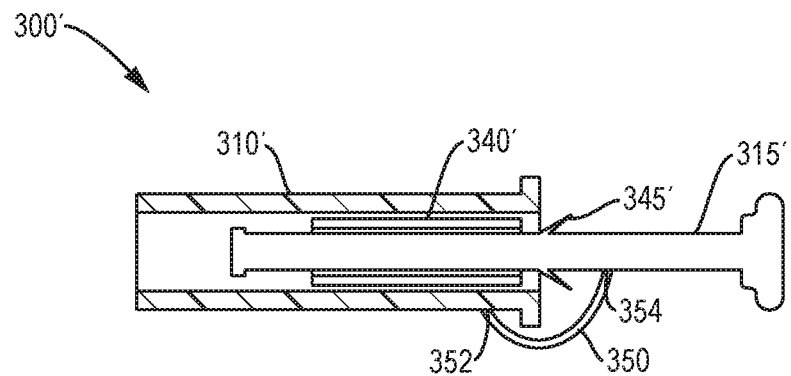
FIG. 3G illustrates an example break-away locking mechanism.
Figure 3H:
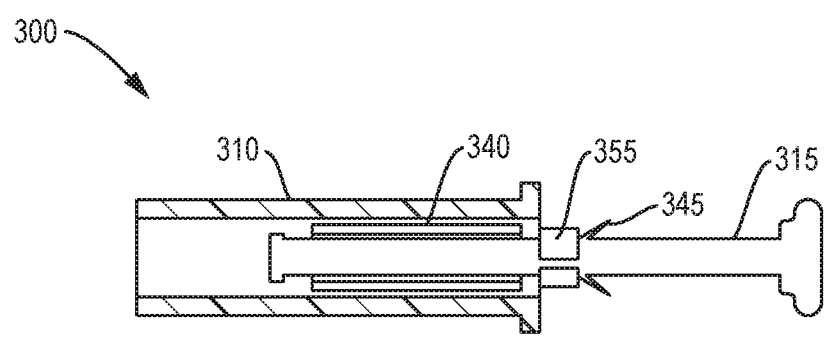
FIG. 3H illustrates an example removable locking mechanism.

FIGS. 3G and 3H illustrate two example components that can prevent the insertion device from locking prematurely by preventing the plunger from moving forward prematurely.

FIG. 3G illustrates insertion device 300' that is similar to device 300, except that a break-away member 350 is provided to couple barrel 310' and plunger 315' of the device. The break-away member 350 keeps the plunger 315' from moving relative to the barrel 310' and, thus, prevents engagement of the disabling feature. The break-away member 350 is configured to break away from the barrel 310' and plunger 315' at break points 352 and 354, respectively. Once the break-away feature is released from the barrel 310' and plunger 315', the plunger can be advanced into the barrel and the disabling feature (e.g., flaps 345') can engage the structural element (e.g., fins 340') of the barrel.

FIG. 3H illustrates a removable cuff 355 applied to the plunger 315 of the device 300. The cuff 355 is sized and shaped to prevent the plunger 315 from moving forward into the barrel 310 until the cuff is removed. This feature can prevent premature engagement of the disabling feature (e.g., flaps 345) with the structural element (e.g., fins 340).

The break-away member 350 and cuff 355 can be made of the same material as the plunger and the barrel, such as plastic, elastomer, paper, or other suitable material. The break-away member 350 and cuff 355 can each be separate component or can be co-manufactured (e.g., co-molded) with the plunger, the barrel, or both. Each mechanism 350, 355 can be configured to be removed by the user, e.g., broken off, torn off, released, etc., when the user is ready to administer the suppository.

Figure 4A:
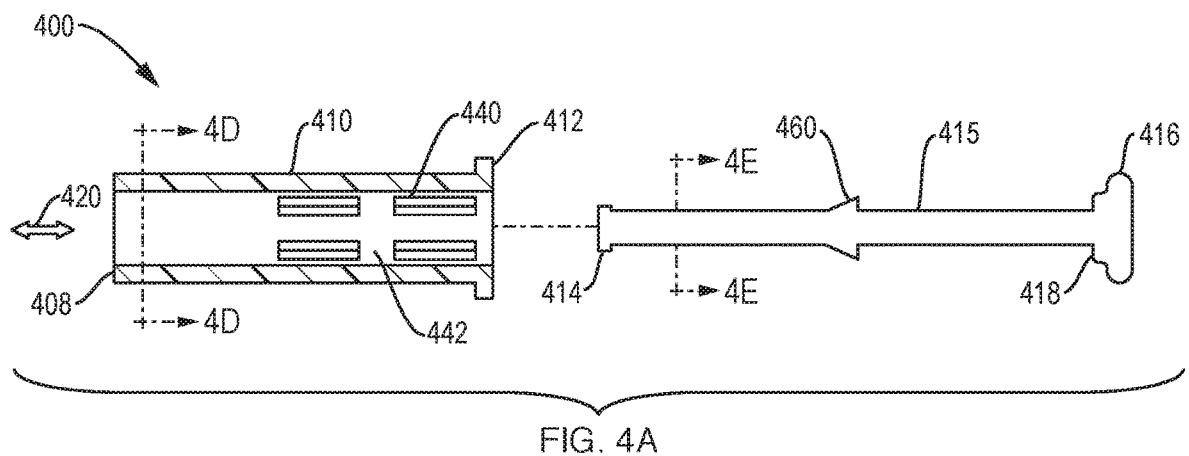
FIG. 4A is a sectional view of a single-use suppository insertion device according to another example embodiment of the invention illustrating the device in an unassembled state.
Figure 4B:
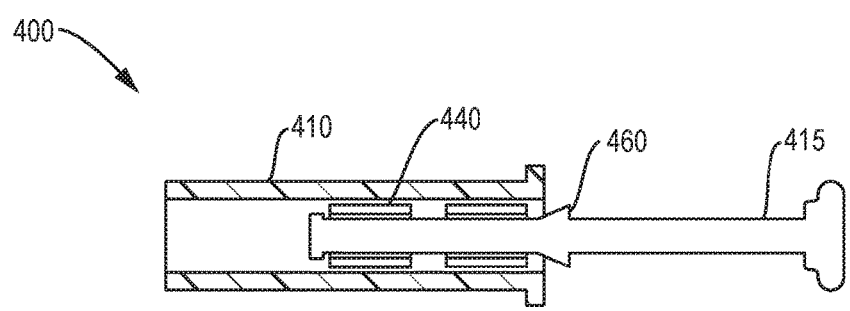
FIG. 4B is a sectional view of the single-use suppository insertion device of FIG. 4A in an assembled state.
Figure 4C:
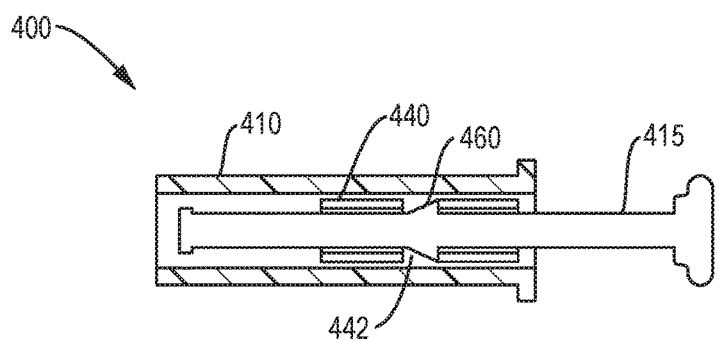
FIG. 4C is a sectional view of the single-use suppository insertion device of FIG. 4B in a locked state.
Figure 4D:
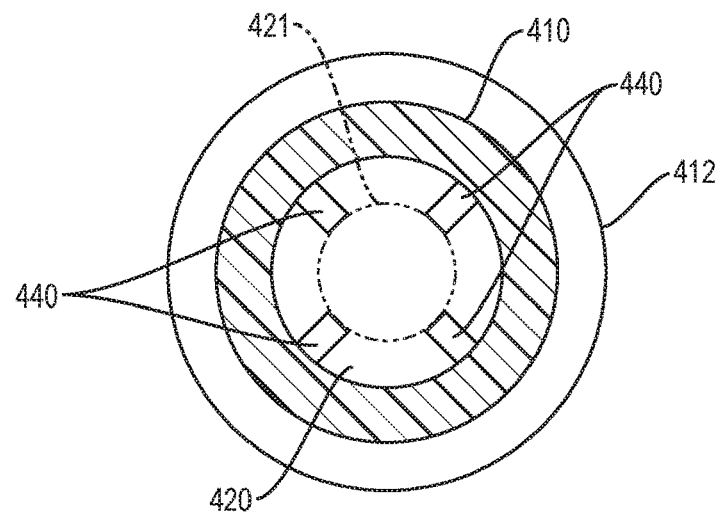
FIG. 4D is a sectional view of the barrel of the device of FIG. 4A.
Figure 4E:
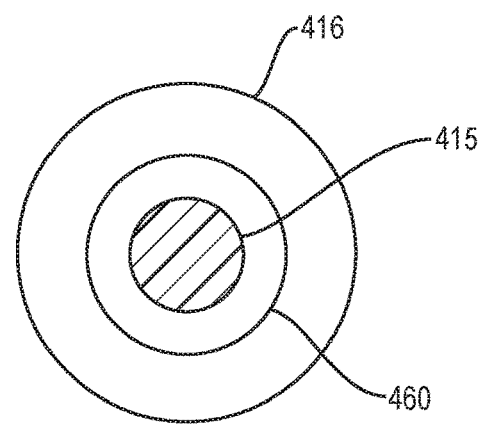
FIG. 4E is a sectional view of the plunger of the device of FIG. 4A.

FIGS. 4A-4E illustrate another example embodiment of a single-use suppository insertion device 400. The device 400 includes a barrel 410 and a plunger 415 that is configured to be movably coupled to the barrel. The barrel 410 include fins 440, which can be spacing elements configured to maintain a gas flow path 420 associated with the device 400, such as gas flow paths described with respect to device 100 of FIG. 1A. As illustrated in FIG. 4D, there can be four fins 440 extending inward from an inside wall of the barrel 410 at equally spaced intervals. The fins 440 can define a space 421 for plunger 415. The plunger 415 includes an insertion end 414, which is wider than a mid-portion of the plunger, and a finger interface end 416, which includes a stepped portion 418 and which may include a cup-shaped interface portion for interfacing with the user's fingertip. A protrusion 460 is positioned along the length of the plunger 415, between the insertion end 414 and the finger interface end 416. In the example shown, the protrusion 460 is a conical-shaped feature (having a triangular cross-sectional profile) that extends outward from an outer surface of the plunger 415, as illustrated in FIG. 4A and in sectional view in FIG. 4E. The protrusion 460 can be formed integrally with the body of the plunger 415. Alternatively, the protrusion 460 can be glued, bonded, or otherwise attached to the body of the plunger 415. The plunger 415 can be solid or hollow and can be configured to define a gas flow path through the plunger, such as is the case with plunger 115 of FIG. 1A.

FIG. 4A shows the device 400 pre-assembly, while FIG. 4B shows the device in an assembled state, where the plunger 415 has been partially inserted into the barrel 410. The insertion portion 414 of the plunger is positioned past the end of the fins 440. The protrusion 460 is positioned at the gripping end 412 of the barrel, before the fins 440.

FIG. 4C illustrates the device 400 locked after first use, the plunger 415 having been advanced further into the barrel 410. As shown, the protrusion 460 is positioned in respective slots 442 of the fins 440. As shown, the plunger 415 is locked in that it cannot be retracted from the barrel 410 because the engagement of the protrusion 460 and the fins 440. The protrusion 460 and the fins 440 can form a ratchet.

Figure 5:
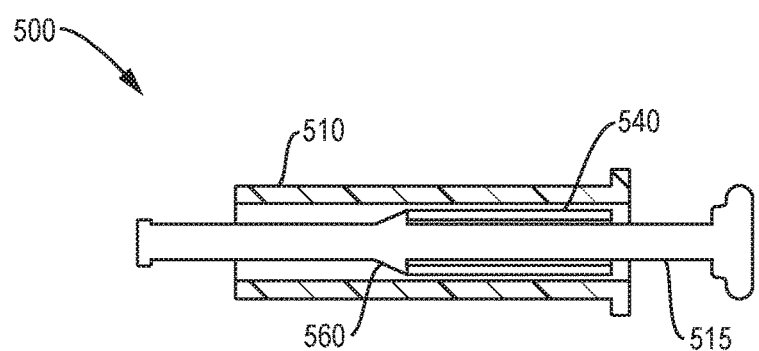
FIG. 5 is a sectional view of a single-use suppository insertion device according to another example embodiment.

FIG. 5 illustrates a single-use suppository insertion device 500 according to another example embodiment. Similar to device 400 of FIGS. 4A-4E, device 500 includes a barrel 510 having fins 540 and also includes a plunger 515 slidably disposed in the barrel and having protrusion 560. In device 500, however, locking of the plunger to the barrel occurs at a different position within the barrel as compared to device 400. Unlike fins 440 of device 400, fins 540 of device 500 do not include a slot to receive protrusion 560. Instead, protrusion 560 engages fins 540 in a locking fashion once the protrusion 560 has been advanced past the end of the fins 540, as illustrated in FIG. 5.

Figure 6A:
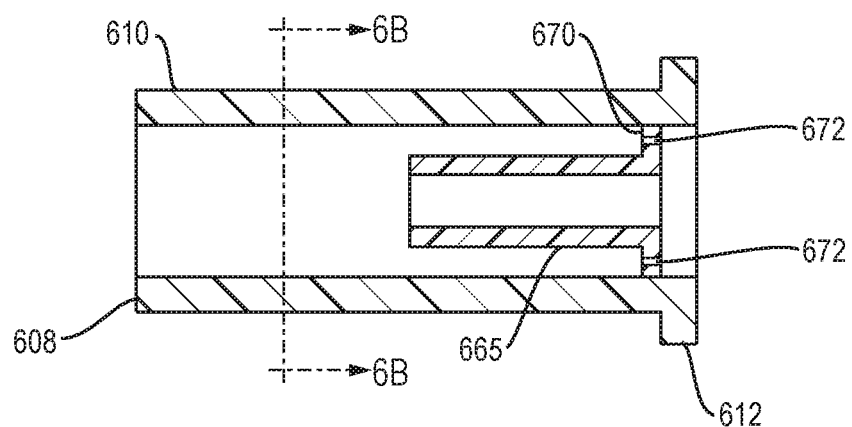
FIG. 6A is a sectional view of a barrel of an insertion device according to another example embodiment.
Figure 6B:
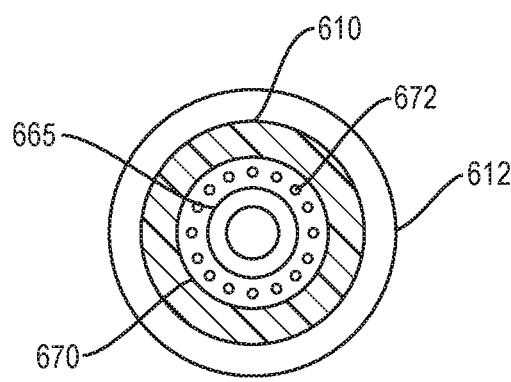
FIG. 6B is a sectional view of the barrel of FIG. 6A illustrating the perforated flange.

FIGS. 6A-6B illustrate a barrel 610 of an insertion device according to another example embodiment. Barrel 610 can be used with any of the plungers described herein, such as plungers 115, 215, 315, 315', 415 and 515. A flange 670 couples a structural element 665 to the barrel 610. Here, the structural element 665 is a spacing element. The flange 670 is configured to break at a perforation 672 (FIG. 6B) of the flange to cause the structural element 665 to uncouple from the barrel 610 when a user attempts to retract the plunger after one-time use of the insertion device. Uncoupling of the element 665 from the barrel 610 is irreversible and renders the device in-operable. For example, the plunger can be coupled to an insert or can include a protrusion or flap, as described herein, to engage the structural element 665. Engagement occurs by movement of the plunger relative to barrel, such as when the user advances the plunger during insertion of the suppository or when the user withdraws the plunger from the suppository. For example, the structural element 665 can break away, such that the plunger is no longer engaged with the barrel. This can leave the plunger to rattle around in the barrel.

Described herein are example embodiments of a single-use suppository insertion device 100, 200, 300, 300', 400, 500 that include a barrel, a plunger and a disabling feature. Embodiments of the single-use suppository insertion device can further include a structural element of the barrel or the plunger configured to engage with the disabling feature of the barrel or the plunger during insertion of or withdrawal away from the suppository to activate the disabling feature. The structural element can be configured to engage irreversibly with the disabling feature and can include a feature complementary to the disabling feature. For example, the complementary feature of the structural element can include a concave surface, and the disabling feature can include a convex surface. The structural element can extend from an inner surface of the barrel and can be a spacing element. The disabling feature can be a protrusion extending outward from an outer surface of the plunger. For example, the disabling feature and the structural element can form a ratchet. The structural element can be coupled to or defined by the barrel, and the disabling feature can be coupled to or defined by the plunger. Engagement of the disabling feature with the structural element can cause the structural element to uncouple from the barrel. The structural element can be configured to engage with the disabling feature during withdrawal of the plunger through the barrel.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A single-use suppository insertion device comprising:
    a barrel sized and shaped to fit within a patient's anal canal;
    a plunger axially movable relative to the barrel and configured to be movably coupled to the barrel;
    a disabling feature of the barrel or the plunger configured to be activated during operational motion of the plunger relative to the barrel and to render the suppository insertion device inoperable after one-time use, the plunger including a mid-portion, an insertion end that is wider than the mid-portion, and a finger interface end, wherein the disabling feature is positioned along the mid-portion of the plunger; and
    a structural element of the barrel or the plunger configured to engage irreversibly with the disabling feature of the barrel or the plunger to activate the disabling feature, wherein the structural element includes plural fins extending from an inner surface of the barrel at radially spaced intervals, each fin extending axially along a length of the barrel.
2. The device of claim 1, wherein the structural element of the barrel or the plunger is configured to engage with the disabling feature of the barrel or the plunger during insertion of or withdrawal away from a suppository to activate the disabling feature.
3. The device of claim 1, wherein the structural element includes four fins extending inward from the inner surface of the barrel at equally spaced intervals.
4. The device of claim 1, wherein the structural element is a spacing element.
5. The device of claim 1, wherein the disabling feature is a protrusion extending outward from an outer surface of the plunger.
6. The device of claim 1, wherein the disabling feature and the structural element form a ratchet.
7. The device of claim 1, wherein the structural element is coupled to or defined by the barrel, and wherein the disabling feature is coupled to or defined by the plunger.
8. The device of claim 1, wherein the structural element is configured to engage with the disabling feature during withdrawal of the plunger through the barrel.
9. The device of claim 1, wherein the structural element extends inward from an inside surface of the barrel and defines a slot to engage with the disabling feature.
10. The device of claim 1, wherein the plunger is hollow.
11. A method for disabling a single-use suppository insertion device after one-time use, the method comprising:
    activating a disabling feature of a barrel or a plunger during operational motion of the plunger relative to the barrel, the barrel being sized and shaped to fit within a patient's anal canal, the plunger being axially movable relative to the barrel and configured to be movably coupled to the barrel, activation of the disabling feature rendering the suppository insertion device inoperable after one-time use, the plunger including a mid-portion, an insertion end that is wider than the mid-portion, and a finger interface end, wherein the disabling feature is positioned along the mid-portion of the plunger, and wherein activating the disabling feature includes irreversibly engaging the disabling feature of the plunger or the barrel with a structural element of the barrel or the plunger during insertion of or withdrawal away from a suppository, wherein the structural element includes plural fins extending from an inner surface of the barrel at radially spaced intervals, each fin extending axially along a length of the barrel.
12. The method of claim 11, wherein the disabling feature of the plunger or the barrel engages with the structural element of the barrel or the plunger during insertion of or withdrawal away from a suppository.
13. The method of claim 11, wherein the structural element includes four fins extending inward from the inner surface of the barrel at equally spaced intervals.
14. The method of claim 11, further comprising spacing the plunger from the barrel by using the structural element as a spacing element.
15. The method of claim 11, further comprising extending a protrusion outward from an outer surface of the plunger to provide the disabling feature.
16. The method of claim 11, further comprising using the disabling feature and the structural element to form a ratchet.
17. The method of claim 11, further comprising coupling the structural element to the barrel or defining the structural element by the barrel, and coupling the disabling feature to the plunger or defining the disabling feature by the plunger.
18. The method of claim 11, wherein activating the disabling feature includes activating the disabling feature during withdrawal of the plunger through the barrel.
19. The method of claim 11, wherein the plunger is hollow.
20. A single-use suppository insertion device comprising:
    a barrel sized and shaped to fit within a patient's anal canal;
    a plunger axially movable relative to the barrel and configured to be movably coupled to the barrel; and means for activating a disabling feature of the plunger or the barrel during operational motion of the plunger relative to the barrel, activation of the disabling feature rendering the suppository insertion device inoperable after one-time use, the plunger including a mid-portion, an insertion end that is wider than the mid-portion, and a finger interface end, wherein the disabling feature is positioned along the mid-portion of the plunger, and wherein the means for activating the disabling feature includes a structural element of the barrel or the plunger configured to engage irreversibly with the disabling feature of the barrel or the plunger, wherein the structural element includes plural fins extending from an inner surface of the barrel at radially spaced intervals, each fin extending axially along a length of the barrel.

21. The device of claim 20, wherein the structural element of the barrel or the plunger is configured to engage with the disabling feature of the barrel or the plunger during insertion of or withdrawal away from a suppository.

22. The device of claim 20, wherein the plunger is hollow.

23. The device of claim 20, wherein the structural element includes four fins extending inward from the inner surface of the barrel at equally spaced intervals.

\* \* \* \* \*